(12) United States Patent
Thys

(10) Patent No.: US 9,782,532 B2
(45) Date of Patent: Oct. 10, 2017

(54) APPARATUS AND METHOD FOR THE VIBRATORY STIMULATION OF AT LEAST ONE PORTION OF A VASCULAR ACCESS DEVICE FOR ITS MONITORING

(75) Inventor: Martin Thys, Grettstadt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1451 days.

(21) Appl. No.: 13/147,879

(22) PCT Filed: Feb. 5, 2010

(86) PCT No.: PCT/EP2010/000724
§ 371 (c)(1),
(2), (4) Date: Aug. 30, 2011

(87) PCT Pub. No.: WO2010/089130
PCT Pub. Date: Aug. 12, 2010

(65) Prior Publication Data
US 2011/0306866 A1    Dec. 15, 2011

(30) Foreign Application Priority Data

Feb. 6, 2009    (DE) .................. 10 2009 007 806

(51) Int. Cl.
*A61M 1/36* (2006.01)
*A61M 5/158* (2006.01)
*A61M 5/168* (2006.01)

(52) U.S. Cl.
CPC ........ *A61M 1/3653* (2013.01); *A61M 1/3656* (2014.02); *A61M 5/158* (2013.01); *A61M 5/16836* (2013.01); *A61M 1/3655* (2013.01); *A61M 2205/13* (2013.01);
(Continued)

(58) Field of Classification Search
USPC ....... 600/437, 439, 459, 461, 462, 464, 466, 600/467
See application file for complete search history.

(56) References Cited

U.S. PATENT DOCUMENTS

| 4,534,756 A | 8/1985 | Nelson |
| 4,648,869 A | 3/1987 | Bobo, Jr. |
| 4,710,163 A | 12/1987 | Butterfield |

(Continued)

FOREIGN PATENT DOCUMENTS

| DE | 37 32 399 C2 | 4/1988 |
| DE | 40 13 402 A1 | 11/1991 |

(Continued)

OTHER PUBLICATIONS

International Search Report WO 2010/089130 A1, mailed Jul. 13, 2010.

(Continued)

*Primary Examiner* — Peter Luong
(74) *Attorney, Agent, or Firm* — Fish & Richardson P.C.

(57) ABSTRACT

The present invention relates to an apparatus for monitoring a vascular access device, including at least one signal generator for generating vibrations in order to stimulate the vascular access device or a portion thereof to vibrate, at least one signal receiver for detecting vibrations of the vascular access device or of said portion thereof, and at least one evaluation device for evaluating the detected vibrations. Moreover a method for monitoring the vascular access device by using the apparatus of the invention is specified.

1 Claim, 2 Drawing Sheets

(52) U.S. Cl.
CPC .............. *A61M 2205/3375* (2013.01); *A61M 2205/3569* (2013.01); *A61M 2205/3592* (2013.01)

(56) References Cited

U.S. PATENT DOCUMENTS

| | | | |
|---|---|---|---|
| 4,794,933 | A | 1/1989 | Yamazaki |
| 4,877,034 | A | 10/1989 | Atkins et al. |
| 5,313,947 | A | 5/1994 | Micco |
| 6,090,048 | A | 7/2000 | Hertz et al. |
| 6,487,428 | B1 | 11/2002 | Culver et al. |
| 2002/0004636 | A1 | 1/2002 | Tsubata |
| 2002/0172323 | A1 | 11/2002 | Karellas et al. |
| 2003/0036713 | A1 | 2/2003 | Bouton et al. |
| 2006/0254982 | A1 | 11/2006 | Kopperschmidt |
| 2008/0195021 | A1 | 8/2008 | Roger et al. |
| 2009/0082676 | A1 | 3/2009 | Bennison |
| 2010/0241024 | A1 | 9/2010 | Koenig |

FOREIGN PATENT DOCUMENTS

| | | |
|---|---|---|
| DE | 92 11 933 U1 | 11/1992 |
| DE | 196 09 698 A1 | 9/1997 |
| DE | 197 34 002 C1 | 9/1998 |
| DE | 197 46 377 C1 | 7/1999 |
| DE | 198 09 945 A1 | 9/1999 |
| DE | 198 48 235 C1 | 3/2000 |
| DE | 100 51 943 A1 | 5/2002 |
| DE | 103 27 261 A1 | 1/2005 |
| DE | 10 2004 023 080 A1 | 12/2005 |
| DE | 10 2006 042 336 A1 | 3/2008 |
| DE | 10 2007 044 413 A1 | 3/2009 |
| DE | 10 2008 013 090 A1 | 9/2009 |
| EP | 0 248 633 A2 | 12/1987 |
| EP | 0 328 162 A2 | 8/1989 |
| EP | 0 330 761 A1 | 9/1989 |
| EP | 0 332 330 A2 | 9/1989 |
| EP | 0911044 A1 | 4/1999 |
| EP | 0943369 A1 | 9/1999 |
| EP | 1199029 A2 | 4/2002 |
| EP | 1 472 973 A1 | 11/2004 |
| EP | 1 595 560 B1 | 9/2009 |
| JP | 2005040518 A | 2/2005 |
| WO | 97/10013 A1 | 3/1997 |
| WO | 99/15074 A1 | 4/1999 |
| WO | 03/002174 A1 | 1/2003 |
| WO | 2004110528 A1 | 12/2004 |
| WO | 2008028653 A2 | 3/2008 |
| WO | 2008/100671 A1 | 8/2008 |
| WO | 2009/038834 A1 | 3/2009 |
| WO | 2009/122229 A1 | 10/2009 |

OTHER PUBLICATIONS

Polaschegg and Levin, 1996, "Replacement of Renal Function by Dialysis" Drukker Parsons and Maher, Kluwer Academic Publishers, Dodrecht, Netherlands, pp. 334-340.

Dolgos et al., Sep. 2009, "Fachpraktikum IS8:Laser-Distanzmessung", Federal Institute of Technology Zurich, Integrated Systems Laboratory, p. 10.

Ziegler, 1998, "Skriptum zur Vorlesung: Physikalische Messtechnik B (Messgroeben): Kapitel E: Geometrie-Messverfahren", University of Paderborn, p. 33.

APPARATUS AND METHOD FOR THE VIBRATORY STIMULATION OF AT LEAST ONE PORTION OF A VASCULAR ACCESS DEVICE FOR ITS MONITORING

CROSS REFERENCE TO RELATED APPLICATIONS

This is a 371 national phase application of PCT/EP2010/000724 filed Feb. 5, 2010, claiming priority to German Patent Application No. 10 2009 007 806.1 filed Feb. 6, 2009.

FIELD OF INVENTION

The present invention relates to an apparatus for the vibratory stimulation of at least one portion of a vascular access device. It furthermore relates to a method for monitoring a vascular access device.

BACKGROUND OF THE INVENTION

Various treatment methods require the utilization of a vascular access device that is adapted to be connected to a patient's vascular system. Such connection is typically effected by introducing at least one portion of the vascular access device into the patient's vascular system. During the treatment method, the connection is ensured by fixation of at least one part of the vascular access device.

Despite safety measures such as the above-mentioned fixation, various causes such as, e.g., movements on the part of the patient may lead to an undesirable disconnection of the vascular access device from the patient's vascular system. Such a disconnection may lead to grave consequences for the patient due to a free flow of blood and should therefore be prevented in a maximum possible degree, or should at least be recognized and corrected as quickly as possible.

From the prior art, various apparatus and methods for recognizing such a disconnection are known.

Thus it is known from practice, for instance, to monitor medical apparatusses through structural/body sound measurements and to make use of changes in the propagation of sound in the apparatus (such as a blood tube system) or in the patient's body in order to detect a disconnection of the vascular access device from the patient's vascular system.

Further methods that are known from practice include the detection of humidity at the location of connection as effected by a leakage of blood.

SUMMARY OF THE INVENTION

It is an object of the present invention to provide another apparatus for monitoring a vascular access device. In addition, it is intended to specify a corresponding method.

The apparatus of the invention is adapted and provided for the vibratory stimulation of at least one portion of a vascular access device or of the entire vascular access device for monitoring the vascular access device.

To this end, the apparatus of the invention includes at least one signal generator for generating vibrations in order to stimulate the vascular access device or said portion thereof to vibrate. It further includes at least one signal receiver for detecting vibrations of the vascular access device or of said portion thereof, and at least one evaluation means for evaluating the detected vibrations.

The signal generator and/or the signal receiver may be a sound generator and receiver. The vibrations may preferably be understood as to be sound waves.

The expression "stimulation of vibration" or "vibratory stimulation" as presently used designates a process wherein a means or at least one portion thereof is made, or is to be made, to vibrate starting up from a first vibratory condition such that it will pass into a second vibratory condition that regularly differs from said first vibratory condition.

Said first vibratory condition may be a rest condition, i.e. a non-vibration, or a starting condition already involving a vibration, for instance at a given frequency and/or amplitude. The second vibratory condition which is attained following stimulation may be a condition of vibrating at a higher frequency and/or a higher amplitude than that of the first vibratory condition.

Moreover such stimulation or such vibratory stimulation may also be a slow-down of vibration of a means that is already in a vibrating state, i.e., it may lead from a first vibratory condition to a second vibratory condition, wherein the second vibratory condition may be characterized by a vibration at a lower frequency and/or a smaller amplitude or by non-vibration.

In accordance with the invention, excitation may thus be any attempt to influence in a particularly intentional manner or to alter—once again in a particularly intentional manner—a vibratory condition.

A "vascular access device" as presently used serves for establishing a fluid communication between an exterior and an interior of any vessel or of some other structure in which a fluid is present either permanently or temporarily. In particular it may preferably serve for establishing a fluid communication between an exterior and an interior of a patient's vascular system. A "patient" within the meaning of the present invention may be either human or animal. At any rate the present invention is, however, not restricted to its application for monitoring a vascular access device for establishing a fluid communication with a patient's vascular system.

A like "fluid communication" may be employed for withdrawing fluids and preferably in particular body fluids such as blood from the vessel or from a patient's vascular system, and/or for introducing fluids into the vessel or into the patient's vascular system.

By means of a fluid communication it is furthermore possible to re-introduce body fluids into the patient's vascular system, e.g. following any treatment and/or purification thereof in an extracorporeal circulation.

Although it may essentially be sufficient to preferentially stimulate vibration of only one portion of the vascular access device by means of the signal generator, it is, of course, also possible for the entire vascular access device to attain a stimulated condition. For the sake of simplicity, the expressions "vascular access device" and "portion of the vascular access device" shall thus in the following be used synonymously for the component stimulated—or to be stimulated—to vibrate.

In this context, both a short-term and a longer-term connection between the vascular access device and the vascular system are considered. The apparatus of the invention can therefore be employed both for indwelling catheters, for example, and for accesses disposed for clearly shorter periods of time, for instance, for the application of an antibiosis.

A "signal generator" as included by the apparatus of the invention may be a piezoelectric or electrodynamic signal generator, however without being restricted thereto.

The latter may—again without being restricted thereto—generate acoustic vibrations for the stimulation of the vascular access device or of a portion thereof.

The signal generator may be disposed in physical proximity of the vascular access device.

The signal output by the signal generator may be employed directly for a vibratory stimulation of the vascular access device, i.e., without any amplification and/or without any modulation or the like.

Moreover it is also possible to transmit the signal output by the signal generator to the vascular access device across a physical distance by using additional suitable means, or to transform energy forms generated by the signal generator into vibrations for stimulating the vascular access device.

A signal receiver of the present apparatus may detect a signal that was retransmitted and/or reflected by the vascular access device.

The signal may be an acoustic signal. The signal may define a vibration or be embodied by such a vibration.

The apparatus of the invention may comprise further means that are suited for such purposes as are named in the foregoing.

Although the present invention occasionally refers to acoustic signals for vibratory stimulation, the present invention is at any rate not restricted to the exclusive use of acoustic signals.

In accordance with the invention, combinations of acoustic signals with signals of other energy forms such as, e.g., temperature, pressure, electric current and any other energy forms appropriate for the purposes of the present invention are likewise considered. Signal generator, signal receiver and additional means may be selected accordingly.

An "evaluation means" as presently employed may be used for evaluating the vibratory signals that are detected by the signal receiver and generated by sound and/or other energy forms.

The evaluated parameters may include frequency and amplitude without being restricted thereto.

The apparatus of the invention serves for monitoring a vascular access device. The apparatus may be configured to monitor a position thereof. It may be configured to monitor a condition of being filled or not being filled, e.g., with a fluid. Combinations of the above-named parameters may equally be monitored in an embodiment of the invention.

By evaluating the detected vibrations, it is possible to infer a positional change of the vascular access device. Such a change may suggest an abnormality of the connection between the vascular access device and the patient's vascular system such as, e.g., a disconnection that has already occurred or is imminent.

By evaluating the detected vibrations, it is possible to infer a filling condition of the vascular access device or a change thereof. Such a change may also suggest an abnormality of the connection between the vascular access device and the patient's vascular system.

A "vascular access device" of a preferred embodiment may be configured, e.g., as a cannula, infusion means or the like, and may allow a longer-term or short-term access to the patient's vascular system.

Corresponding vascular access devices may be selected depending on the application and include commercially available one-way articles.

Such vascular access devices may be formed of metals, synthetic materials, shape memory alloys, electrical insulators, and the like.

The vascular access device may be suited for establishing a fluid communication with a shunt, a fistula, an arterial or venous vessel of the patient.

A "portion of a vascular access device" may, e.g., be a punction means or puncture means, respectively, such as a punction needle, a punction wing, e.g., an arterial or venous connection needle of a Double-Needle access for an extracorporeal blood treatment or the needle of a Single-Needle access or a catheter or any other means adapted to be introduced at least partially into the patient's vascular system in order to establish a connection between the vascular access device and the former and thus admit an access to the patient's vascular system, and may furthermore be portions, areas or partial areas thereof.

As was set forth in the foregoing, the "patient's vascular system" may presently be understood as the patient's blood circulation in the sense of an anatomical structure including arterial and venous conduit structures of the body or portions thereof.

The vascular access device may be suited and provided for performing a treatment method. "Treatment method" within the meaning of the present invention encompasses any customary methods for treating a patient which may be performed by using a vascular access device adapted to be connected to the patient's vascular system, or which require such a vascular access device. Without being restricted thereto, such methods may include extracorporeal blood treatment methods such as hemodialysis, hemofiltration, hemodiafiltration, but also cell separation methods, apheresis, medications, and the like.

The expression "the exterior" may be understood as any areas outside of the vessel, in particular extracorporeal areas or means that are suited for receiving a fluid to be withdrawn from the vessel and in particular from a patient's vascular system and/or to be introduced and/or re-introduced into the patient's vascular system. Examples include storage devices such as bags holding liquids, in particular substituate fluids such as isotonic saline solution, e.g. 0.9% NaCl solution, other infusion solutions, portions of extracorporeal blood circulations for a treatment of the patient's blood such as, e.g., portions of an extracorporeal tubing system, devices holding drugs for the administration thereof, and the like.

The exterior may also designate the atmosphere.

The apparatus of the invention may be suited for monitoring a connection, in particular a venous connection, for example during a process of removing blood from an extracorporeal blood circulation for a treatment apparatus following termination of a blood treatment session, where the vascular access device has already been disconnected from a patient's vascular system and a fluid communication thus does not exist any more.

If deemed appropriate, the signal detected by the signal receiver may be amplified, attenuated, transmitted and/or deflected prior to its evaluation.

The evaluation means may be coupled—in particular directly—to the signal generator and/or to the signal receiver and/or may physically be connected to the latter.

The evaluation means may be configured to automatically perform the evaluation at particular intervals or continuously.

The evaluation means may be present at the patient and/or in or on a "treatment apparatus" for performing a treatment method and may be disposed in a manner fixedly integrated with it or in a replaceable manner. A treatment apparatus within the meaning of the present invention may be an apparatus for performing one of the above-named exemplary treatment methods such as, e.g., a dialysis apparatus.

"Evaluation" of the detected vibrations may take place in an analog or digital manner and may be based on empirical values and/or on previously detected vibration patterns.

Evaluation may take place in a manually controlled or automated manner, e.g., with the aid of a corresponding software program.

In another preferred embodiment, the evaluation means of the apparatus of the invention is adapted to evaluate a vibratory characteristic and/or a mechanical attenuation and/or a decay characteristic of the vascular access device or of said portion thereof.

Moreover, the evaluation means may be prepared and suited for carrying out an analysis by evaluating an energy absorbed by the signal transmitter.

This may in particular be performed if a vibrating body or vibrating system is stimulated periodically at a low frequency and the frequency is increased continuously ("sweep").

When the frequency of stimulation approaches the natural frequency/frequencies of the vibrating body or vibrating system (resonance) and the amplitude of the signal transmitter is delimited, the vibrating body will generally absorb a smaller amount of energy. For example in the case of an electrodynamic signal generator or stimulator, a lower current will be conducted at a constant voltage amplitude of the signal generator or stimulator, respectively, in the vicinity of resonance. This is due to the impedance of the signal generator rising to a maximum.

As will also be explained in the following with reference to the figures and in particular to FIG. 4 of the drawing, such a change of the energy absorbed by the signal transmitter may correspond to a change of the vibratory characteristic and thus allow conclusions concerning the connection of a vascular access device. Thereby, it is possible to utilize the effect of an "enforced vibration."

Means for storing and/or recording the detected vibratory signals, a vibratory characteristic, such as for example a decay characteristic and/or previously detected vibration patterns may be connected to the evaluation means or other portions of the apparatus of the invention either permanently or only at desired time points.

The expression "vibratory characteristic" may be understood as to be a currently detected vibratory condition that should be evaluated as the in fact detected vibratory condition, and/or as a succession of different vibratory conditions in a—particularly brief—time interval, or as changes of vibrations (relative and/or over time), whereas the expression "vibration pattern" designates a vibratory characteristic of the vascular access device during a particular treatment method that is necessary for a correct functioning and as such may represent a characteristic quantity of a particular treatment method and/or of a particular vascular access device.

In a preferred embodiment of the present invention, the signal generator and the signal receiver are physically interconnected in a structure.

The expression "physically interconnected" means that the signal generator and the signal receiver may be disposed on a common support structure and/or inside a common housing.

In a development of the present invention, the signal generator and the signal receiver are physically interconnected, in other words, the two means are in contact with each other through frictional, form closure and/or material connections.

The signal generator and the signal receiver may be realised as two means or may be present in one common means.

In a further preferred embodiment of the apparatus of the invention, the signal generator and the signal receiver are provided and adapted for being arranged on the vascular access device.

Such arrangement may include a permanent or releasable connection.

In a further preferred development, the apparatus of the invention moreover comprises a fastening means for fastening the apparatus or parts thereof to the vascular access device.

A like fastening means may, e.g., include a support structure and/or a housing and additional means for frictional and/or form closure fastening of the apparatus of the invention to the vascular access device.

The fastening means may likewise include through holes, lugs and the like for a permanent or releasable connection of the fastening means to the vascular access device.

In preferred developments, the fastening means may have the form of a clip, clasp or sleeve or the like. A clasp may be configured so as to allow its fastening to a punction means, e.g. a cannula, following punction of a vessel.

Materials that are particularly suited for this purpose may include synthetic materials, metals, composite materials and the like that are adapted not to influence, for instance not to falsify, the vibratory signals and/or generation, detection and/or evaluation thereof.

The fastening means may have any desired shape. It is preferably configured in order to allow the transmission of vibrations from the signal generator and/or signal receiver connected thereto to the vascular access device, or detection thereof by the latter.

A further preferred embodiment includes the connection of the evaluation means to the signal generator and/or the signal receiver by using a conductor such as, e.g., an electric cable.

In another embodiment, the evaluation means may moreover be in wireless communicative connection with the signal generator and/or the signal receiver. This includes, e.g., a communicative connection by way of infrared, RFID (Radio Frequency Identification; identification by means of electromagnetic waves), Bluetooth, WLAN and the like, if deemed appropriate for the purposes of the present invention.

The apparatus of the invention may comprise the respective necessary means for generating and ensuring a like communicative connection.

In another further preferred embodiment, the apparatus of the invention includes a means for editing or processing the received signals. Such means may be adapted, e.g., for filtering, averaging the received signals and/or for noise suppression and the like.

A further preferred embodiment includes a means provided for determining an attenuation of the vibratory signals emitted by the vascular access device or a vibratory characteristic of the latter.

In a means of a further preferred development of the present invention, an attenuation or an attenuation pattern may moreover be compared to known attenuations such as, e.g., a known attenuation pattern, with the help of corresponding means.

The apparatus of the invention may preferably comprise a means for comparing a determined vibratory characteristic or a vibration pattern to known vibratory characteristics or vibration patterns, respectively, as provided by a further preferred embodiment.

Processing of the received signals, determination of an attenuation, comparison of the attenuation to a known attenuation and/or comparison of a vibratory characteristic to a known vibratory characteristic may likewise be performed in the evaluation means of the apparatus of the invention.

Moreover the vibrational and/or attenuation patterns may be stored in the evaluation means by using suitable memory means.

Such a means may be configured, e.g., in the form of an electronic means such as, for example, a chip or some other data processing means.

The apparatus according to the present invention may include additional means. These include, e.g., means for outputting an acoustic and/or optical signal such as, for example, an alarm signal, means for (closed- and/or open-loop) control of fluid communications of the treatment apparatus based on the result of monitoring or based on the detected and optionally evaluated signals and/or the vascular access device, such as, e.g., blocking means, e.g. clamps such as an arterial and/or venous tube clamp of an extracorporeal blood treatment apparatus, shut-off valves, stop means, e.g. (closed- and/or open-loop) control means and/or stop switches and the like for stopping a fluid conveying means such as, for example, an arterial blood pump, and the like.

A further preferred embodiment includes a (closed- and/or open-loop) control means for influencing the supply of a medium via the vascular access device. Such a (closed- and/or open-loop) control means may, e.g., be connected to an above-mentioned blocking and/or stop means and corresponding means for determining and evaluating predetermined threshold values for supplying or not supplying a medium. The "medium" may include blood, a substituate fluid, an infusion solution, drug solutions and the like.

The means of the apparatus of the invention may be automated means and may be interconnected via additional (closed- and/or open-loop) control means.

A preferred embodiment further includes a communicative connection for connecting the signal generator and/or the signal receiver to the evaluation means and/or to a treatment apparatus such as, e.g., a blood treatment apparatus, e.g. a dialysis apparatus.

In a preferred embodiment, the vascular access device is a punction means or an infusion means.

The apparatus of the invention may further include a like vascular access device. Here, the vascular access device may preferably include an electrically insulating material or be comprised thereof. It may be sufficient if only the one portion of the vascular access device that is of interest for vibratory stimulation is comprised of an electrically insulating material or includes such a material, e.g. in form of a coating.

As the method of the invention may be carried out by using the above-named apparatus of the invention, reference is made to the embodiments described in the foregoing in order to avoid repetitions.

The present invention may advantageously be employed for monitoring a vascular access device in a simple manner while involving low complexity in terms of technology and apparatus.

Evaluation of the vibratory signals received by the vascular access device allows one to infer a current position thereof. Thus, it is advantageously possible to recognize a positional change or even slipping out of the portion of the vascular access device being/having been introduced into the patient's vascular system. Accordingly, preventive measures may be taken. If such an abnormal condition should already have occurred, the present invention can enable rapid action by the treatment personnel and may thus in a given case prevent the possibility of a patient suffering grave consequences.

This may be of particular advantage in the case of an extracorporeal blood treatment where an unnotified slipping out of a connection needle from the patient's vascular system can lead to a loss of blood or a bleeding to death of the patient.

By providing means that are in communicative connection with each other, such as evaluation means, signal generating means, blocking and/or stop means, a free flow of the patient's blood into the environment may advantageously be stopped.

Alarm means may furthermore contribute to a reliable discrimination of an abnormal condition and may call the attention of treatment personnel not sojourning in immediate vicinity.

The present apparatus may advantageously detect the attenuation condition of a vascular access device and compare it to known attenuation patterns. This does not necessarily require the introduction of a portion of the vascular access device into the vessel and in particular into the patient's vascular system. In this way, the present monitoring may, e.g., be carried out independently from a patient's presence. Monitoring of the vascular access device, e.g. of the needle, may even be carried out in cases where the latter is not connected.

Under particular circumstances an abnormal condition may even be inferred if the vibratory characteristic to be expected on the basis of known vibrational or attenuation patterns fails to appear; as a result it is also possible, e.g., to recognize, for example, the fact that the monitored vascular access device has not yet been connected to a patient's vascular system prior to the patient's treatment. It can likewise be possible in the disconnected condition of the vascular access device to recognize whether the vascular access device, or a portion thereof, has already been filled with a liquid.

By means of the apparatus in accordance with the present invention it is advantageously possible to even recognize an inadvertent loosening of the signal generator and/or of the signal receiver from the vascular access device.

Inasmuch as fastening means such as clip, clasp or sleeve for receiving the apparatus of the invention may be fastened to the vascular access device in a releasable manner, they may advantageously be combined with one-way vascular access devices such as punction wings, punction needles or whole blood tube sets and thus be re-usable repeatedly. This contributes to the avoidance of costs for manufacture and logistics such as, e.g., transport and store-keeping. It is furthermore advantageously possible to continue using the known one-way vascular access devices without having to modify them.

In contrast with monitoring the acoustic or electrical conductivity of a "vessel loop" in cases of two vascular accesses as known from the prior art, the present invention also allows to monitor a fluid system having only one vascular access. As one example, a Single-Needle method may be mentioned.

If the vascular access device is made of an electrically insulating material or includes such a material in a corresponding location, the present invention offers another advantage to the effect that monitoring is still possible while it is not possible with prior-art methods that rely on the integrity of an electric circuit by incorporating an electrically conductive cannula for recognizing a disconnection.

Even an abrupt removal of a needle from a vessel is detected securely. The apparatus of the invention herein advantageously differs from systems that are based on the detection of humidity owing to a leakage of blood. Namely, in the case of abrupt removal, for instance when the patient turns in the bed, the open jet of blood might possibly not even hit the humidity sensor that is attached to the needle. An attenuation or an altered vibratory characteristic will otherwise also be detected in such a case.

Generally, the apparatus of the invention can advantageously measure the attenuation condition or the attenuation of a vascular access device including, for example, a cannula, a wing, a tube and a strip of tape. This may advantageously be employed for recognizing an arterial or venous needle disconnection just like for recognizing the disconnection of an infusion needle and for several other purposes.

By using the apparatus of the invention it is thus advantageously possible to even recognize an imminent disconnection due, e.g., a loosening of the fixation of the vascular access device to the patient being released, or to a positional change of the vascular access device.

BRIEF DESCRIPTION OF THE DRAWINGS

The present invention will in the following be described by way of preferred embodiments with reference to the appended drawings, in which like reference numerals are used for designating like elements. In the drawings.

DETAILED DESCRIPTION OF THE DRAWINGS

Figure 1:
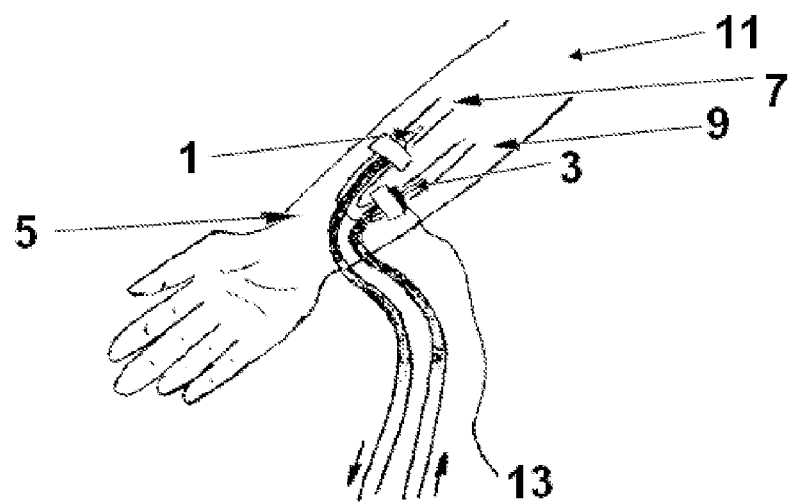
FIG. 1 shows in a schematically simplified manner a possible arrangement of the apparatus of the invention.

FIG. 1 shows an arterial connection needle 1 and a venous connection needle 3 which serve as examples of vascular access devices being connected with a shunt 5 between an artery 7 and a vein 9 of the vascular system of a patient 11. An apparatus of the invention 13 is attached to the venous connection needle 3.

Figure 2:
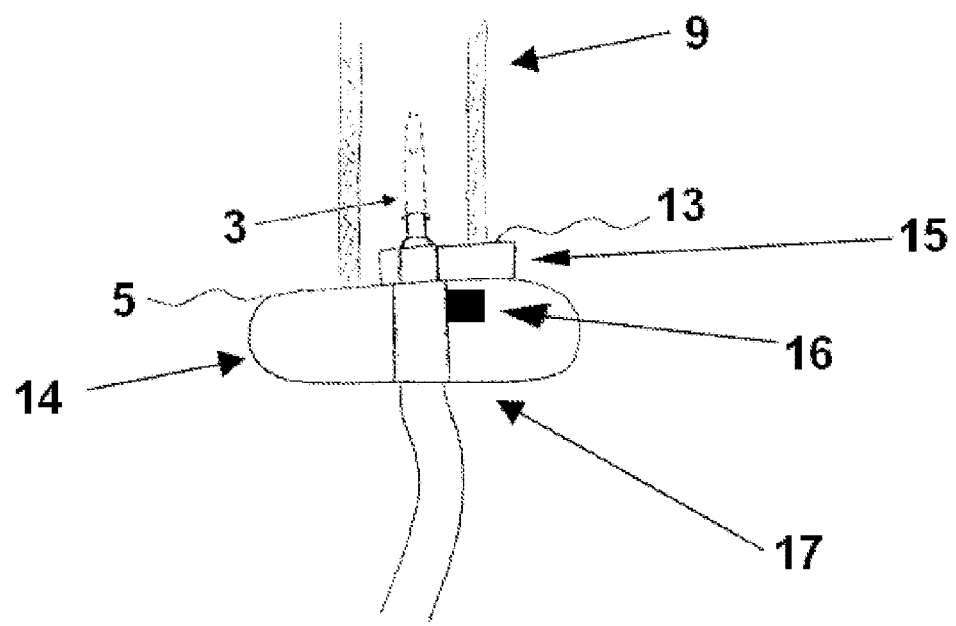
FIG. 2 shows in a schematically simplified manner an embodiment of the apparatus of the invention in enlarged view.

FIG. 2 shows in an enlarged view an apparatus of the invention 13 wherein a signal generator/signal receiver 15 and an evaluation means 16 are fastened to a clip 17 and the latter is connected to the venous connection needle 3. Moreover a vascular access device 5 provided with a so-called punction or butterfly wing 14 is illustrated. The signal generator/signal receiver 15 is presently illustrated as a common means having the functions of both "transmitting" and "receiving." The two functions may, however, also be realized with two separate means.

Figure 3:
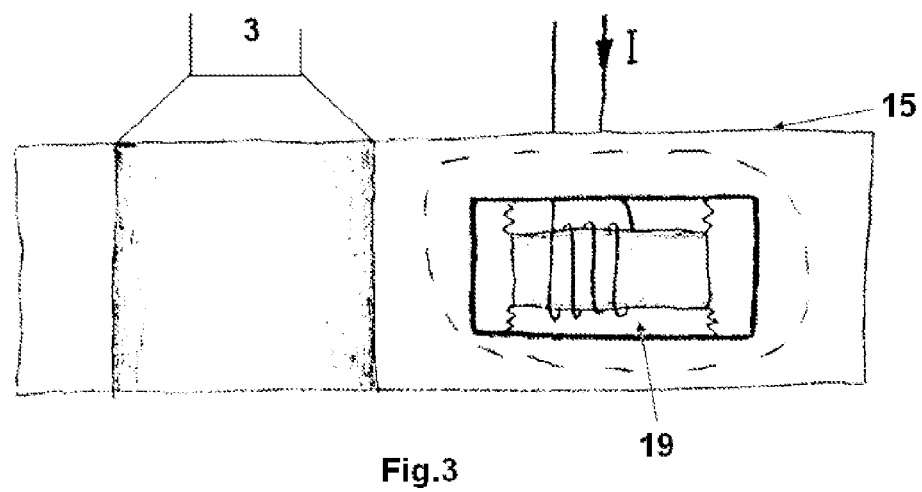
FIG. 3 is an enlarged view of another embodiment of the apparatus of the invention.

FIG. 3 shows an enlarged view of the apparatus of the invention 13, wherein the signal generator/signal receiver 15 comprises an electrodynamic transducer 19. It is, for example, possible to record both the energy quantities absorbed by a signal generator and the vibratory signals received by a signal receiver. Acoustic signals received by the signal generator/signal receiver 15 may be converted into electric signals and evaluated by an evaluation means.

Figure 4:
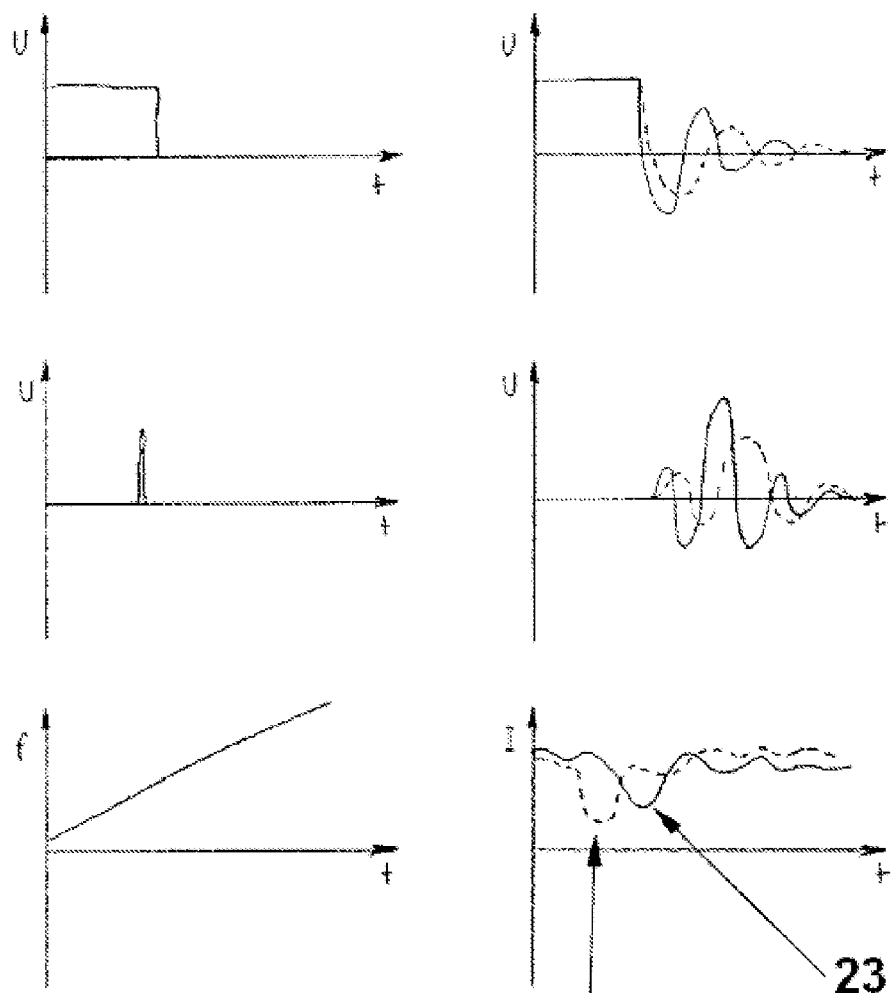
FIG. 4 shows schematic graphs during monitoring of a vascular access device by using the apparatus of the invention.

FIG. 4 shows schematic graphs representing the monitoring of a vascular access device by using the present apparatus. The graphs do not depict actual measurements but show the measured results schematically. In the left-hand column of FIG. 4, the electronic signals emitted by the signal receiver 15 are represented as a voltage U per time unit t and/or as a frequency f per time unit t. The right-hand column shows the signals received by an evaluation means of the apparatus of the invention. The graphs are matched in lines, i.e., the left-hand graphs show the emitted signals (input signal), and the respective right-hand graphs show the corresponding received signals (output signals). The graphs represented in dashed lines each show signals of a needle about to slip out and/or having lost its optimum fixation.

Line 1 of FIG. 4 illustrates the use of a transceiver, for example an electrodynamic transducer. The input signal is a step signal; the output signal is the associated step response.

Line 2 of FIG. 4 illustrates the use of discrete transmitter and receiver, for example an electrodynamic transducer. The input signal is a pulse; the output signal is the associated pulse response.

Line 3 of FIG. 4 illustrates the use of a transceiver, for example an electrodynamic transducer. The left-hand graph shows a so-called "frequency sweep" for the input signal. The right-hand graph shows the associated output signal as a function of the absorbed current in the case of a sweep with a constant voltage amplitude at the transceiver as a "signal to be evaluated." The dashed signal 21 illustrates the slipping out of a connection needle 1, 3. The signal 23 drawn as a solid line illustrates a correct connection.

The present invention is not restricted to the embodiments described in the foregoing; these merely serve for illustrative purposes.

The invention claimed is:

1. A method for monitoring a vascular access device, comprising:
   generating, via at least one signal generator, vibrations in order to stimulate the vascular access device or a portion thereof to vibrate;
   detecting, via at least one signal receiver, vibrations of the vascular access device or of said portion thereof; and
   evaluating, via at least one processor, the detected vibrations.

* * * * *